US008088405B2

(12) United States Patent
Uhrich

(10) Patent No.: US 8,088,405 B2
(45) Date of Patent: Jan. 3, 2012

(54) THERAPEUTIC COMPOSITIONS AND METHODS

(75) Inventor: Kathryn E. Uhrich, Plainfield, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 762 days.

(21) Appl. No.: 11/524,664

(22) Filed: Sep. 21, 2006

(65) Prior Publication Data

US 2007/0014832 A1    Jan. 18, 2007

Related U.S. Application Data

(63) Continuation of application No. 10/368,288, filed on Feb. 18, 2003, now abandoned, which is a continuation of application No. PCT/US00/33378, filed on Dec. 7, 2000, and a continuation of application No. 09/732,516, filed on Dec. 7, 2000, now Pat. No. 6,685,928.

(60) Provisional application No. 60/304,190, filed on Dec. 7, 1999.

(51) Int. Cl.
*A61F 2/02* (2006.01)
*A61K 31/415* (2006.01)
*A61K 31/365* (2006.01)

(52) U.S. Cl. .................. 424/426; 514/406; 514/471

(58) Field of Classification Search .................. None
See application file for complete search history.

(56) References Cited

U.S. PATENT DOCUMENTS

| | | | |
|---|---|---|---|
| 4,062,855 A | 12/1977 | Allan et al. | |
| 4,126,445 A | 11/1978 | Allan et al. | |
| 4,190,716 A | 2/1980 | Parkinson et al. | |
| 4,298,595 A | 11/1981 | Parkinson et al. | |
| 4,375,968 A | 3/1983 | Manhart | |
| 4,414,203 A | 11/1983 | Cabardo, Jr. | |
| 4,612,302 A | 9/1986 | Szabo et al. | |
| 4,684,620 A | 8/1987 | Hruby et al. | |
| 4,757,128 A | 7/1988 | Domb et al. | |
| 4,792,598 A | 12/1988 | Ziegast | |
| 4,857,311 A | 8/1989 | Domb et al. | |
| 4,868,274 A | 9/1989 | Gupta et al. | |
| 4,886,870 A | 12/1989 | D'Amore et al. | |
| 4,888,176 A | 12/1989 | Langer et al. | |
| 4,891,225 A | 1/1990 | Langer et al. | |
| 4,906,474 A | 3/1990 | Langer et al. | |
| 4,938,949 A | 7/1990 | Borch et al. | |
| 4,997,904 A | 3/1991 | Domb | |
| 4,999,417 A | 3/1991 | Domb | |
| 5,082,925 A | 1/1992 | Shalaby et al. | |
| 5,175,235 A | 12/1992 | Domb et al. | |
| 5,259,968 A | 11/1993 | Emert et al. | |
| 5,264,540 A | 11/1993 | Cooper et al. | |
| 5,321,113 A * | 6/1994 | Cooper et al. | 528/176 |
| 5,364,725 A | 11/1994 | Wilson et al. | |
| 5,498,729 A | 3/1996 | Domb | |
| 5,514,764 A | 5/1996 | Frechet et al. | |
| 5,518,730 A | 5/1996 | Fuisz | |
| 5,545,409 A | 8/1996 | Laurencin et al. | |
| 5,599,552 A * | 2/1997 | Dunn et al. | 424/423 |
| 5,610,241 A * | 3/1997 | Lee et al. | 525/411 |
| 5,629,009 A | 5/1997 | Laurencin et al. | |
| 5,639,468 A | 6/1997 | Rodgers et al. | |
| 5,660,851 A | 8/1997 | Domb | |
| 5,798,115 A | 8/1998 | Santerre et al. | |
| 5,837,278 A | 11/1998 | Geistlich et al. | |
| 5,889,028 A | 3/1999 | Sandborn | |
| 5,891,477 A | 4/1999 | Lanza et al. | |
| 5,902,110 A * | 5/1999 | Alfano et al. | 433/215 |
| 5,902,599 A | 5/1999 | Anseth et al. | |
| 5,942,252 A | 8/1999 | Tice et al. | |
| 5,958,911 A | 9/1999 | Evans et al. | |
| 5,990,109 A * | 11/1999 | Chen et al. | 514/250 |
| 6,051,255 A | 4/2000 | Conley et al. | |
| 6,071,530 A | 6/2000 | Polson et al. | |
| 6,153,212 A | 11/2000 | Mao et al. | |
| 6,403,675 B1 * | 6/2002 | Dang et al. | 523/113 |
| 6,468,519 B1 | 10/2002 | Uhrich | |
| 6,486,214 B1 | 11/2002 | Uhrich | |
| 6,602,915 B2 | 8/2003 | Uhrich | |
| 6,613,807 B2 | 9/2003 | Uhrich | |
| 6,685,928 B2 | 2/2004 | Uhrich et al. | |
| 6,689,350 B2 | 2/2004 | Uhrich | |
| 7,122,615 B1 | 10/2006 | Uhrich | |
| 7,396,527 B2 | 7/2008 | Uhrich | |
| 7,411,031 B2 | 8/2008 | Uhrich et al. | |

(Continued)

FOREIGN PATENT DOCUMENTS

AU        750424 B2    3/2003

(Continued)

OTHER PUBLICATIONS

Ulf Lerner "Indomethacin Inhibits Bone Resoprtion and Lysosomal Enzyme Release from Bone in Organ Culture". Scandinavian Journal of Rheumatology vol. 9, No. 3, pp. 149-156 1980.*

Anastasiuou, , "Synthesis of Novel, Degradable Polyanhydries Containing Para-Aminosalicyclic Acid as Drug Delivery Devices for Tuberculosis Treatment", *Polymer Preprints*, 41(2), 1366-1367 (2000).

Anastasiou, Theodore J., et al., "Novel Polyanhydries with Enhanced Thermal and Solubility Properties", *Macromolecules*, 33(17), (2000), 6217-6221.

Anastasiou, Theodore J., et al., "Novel, Degradable Polyanhydrides", *25th Annual Meeting Transactions of the Society for Biomaterials*, Abstract, (1999), 79.

Attawia, Mohamed A., et al., "Biocompatibility Testing of Poly(anhydride-co-imides) Containing Pyromeilitylimidoalanine", *The 21st Annual Meeting of the Society for Biomaterials*, Abstract, (Apr. 5-9, 1994), 222.

(Continued)

*Primary Examiner* — Robert A Wax
*Assistant Examiner* — Danah Al-Awadi
(74) *Attorney, Agent, or Firm* — Viksnins Harris & Padys PLLP

(57) ABSTRACT

Methods of promoting healing through enhanced regeneration of tissue (e.g. hard tissue or soft tissue) by contacting the tissue or the surrounding tissue with an anti-inflammatory agent. These methods are useful in a variety of dental and orthopedic applications.

14 Claims, 1 Drawing Sheet

U.S. PATENT DOCUMENTS

| | | | |
|---|---|---|---|
| 7,534,852 B2 | 5/2009 | Uhrich | |
| 7,662,864 B2 | 2/2010 | Kanamathareddy et al. | |
| 7,666,398 B2 | 2/2010 | Uhrich | |
| 2003/0035787 A1 | 2/2003 | Uhrich | |
| 2004/0038948 A1 | 2/2004 | Uhrich | |
| 2004/0044125 A1 | 3/2004 | Uhrich | |
| 2004/0096476 A1 | 5/2004 | Uhrich et al. | |
| 2005/0031577 A1 | 2/2005 | Uhrich | |
| 2005/0053577 A1 | 3/2005 | Uhrich | |
| 2005/0089504 A1 | 4/2005 | Uhrich | |
| 2005/0089506 A1 | 4/2005 | Uhrich | |
| 2005/0100526 A1 | 5/2005 | Uhrich et al. | |
| 2005/0131199 A1 | 6/2005 | Uhrich et al. | |
| 2005/0249697 A1 | 11/2005 | Uhrich et al. | |
| 2006/0013851 A1 | 1/2006 | Giroux | |
| 2006/0039964 A1 | 2/2006 | Uhrich et al. | |
| 2006/0057179 A1 | 3/2006 | Giroux | |
| 2006/0188546 A1 | 8/2006 | Giroux | |
| 2007/0098800 A1 | 5/2007 | Giroux et al. | |
| 2007/0196417 A1 | 8/2007 | Uhrich | |
| 2008/0226583 A1 | 9/2008 | Uhrich | |
| 2008/0233078 A1 | 9/2008 | Uhrich | |
| 2009/0035248 A1 | 2/2009 | Uhrich et al. | |
| 2010/0074937 A1 | 3/2010 | Uhrich | |
| 2010/0152410 A1 | 6/2010 | East et al. | |
| 2010/0272670 A1 | 10/2010 | Uhrich et al. | |
| 2010/0291180 A1 | 11/2010 | Uhrich | |
| 2010/0291181 A1 | 11/2010 | Uhrich et al. | |
| 2010/0310498 A1 | 12/2010 | Kanamathareddy et al. | |
| 2011/0022161 A1 | 1/2011 | Uhrich et al. | |

FOREIGN PATENT DOCUMENTS

| | | |
|---|---|---|
| CA | 2393676 A1 | 7/2002 |
| DE | 288311 | 3/1991 |
| DE | 288387 | 3/1991 |
| EP | 0246341 A1 | 11/1987 |
| EP | 0 483 429 | 5/1992 |
| EP | 0580386 A1 | 1/1994 |
| JP | 60255797 A | 12/1985 |
| JP | 61186309 A | 8/1986 |
| NL | 9000237 | 8/1991 |
| WO | WO 99/12990 | 3/1990 |
| WO | WO-90/09779 A1 | 9/1990 |
| WO | WO-91/09831 A1 | 7/1991 |
| WO | WO 91/18940 | 12/1991 |
| WO | WO-97/39738 A2 | 10/1997 |
| WO | WO-97/44016 A1 | 11/1997 |
| WO | WO-98/36013 A1 | 8/1998 |
| WO | WO 00/12990 * | 10/1998 |
| WO | WO 98/43554 | 10/1998 |
| WO | WO 99/012990 * | 10/1998 |
| WO | WO-99/12990 A1 | 3/1999 |
| WO | WO-99/29885 A1 | 6/1999 |
| WO | WO-01/28492 A2 | 4/2001 |
| WO | WO-01/41753 A2 | 6/2001 |
| WO | WO-02/09767 A2 | 2/2002 |
| WO | WO-02/09768 A2 | 2/2002 |
| WO | WO-02/09769 A2 | 2/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 2004/006863 | 1/2004 |
| WO | WO 2004/039355 | 5/2004 |
| WO | WO 2004/045549 | 6/2004 |
| WO | WO 2005/039489 | 5/2005 |
| WO | WO 2005/042600 | 5/2005 |
| WO | WO 2006/127667 | 11/2006 |
| WO | WO 2007/143698 | 12/2007 |
| WO | WO 2008/034019 | 3/2008 |
| WO | WO 2008/103744 | 8/2008 |
| WO | WO 2008/128193 | 10/2008 |
| WO | WO 2009/026544 | 2/2009 |

OTHER PUBLICATIONS

Attawia, Mohamed A., et al., "Cytotoxicity testing of poly(anhydride-co-imides) for orthopedic applications", *Journal of Biomedical Materials Research*, 29(10), (1995), 1233-1240.

Attawia, Mohamed A., et al., "In vitro bone biocompatibility of poly (anhydride-co-imides) containing pyromellitylimidoalanine", *Journal of Orthopedic Research*, 14(3), (1996), 445-454.

Attawia, Mohamed A., et al., "Proliferation, Morphology, Expression by Osteoblasts Cultured on Poly(anhydride-co-amides)", *Journal of Biomedical Materials Research*, 48(3), (1999), 322-327.

Attawia, Mohamed A., et al., "Regional drug delivery with radiation for the treatment of Ewing's sarcoma—in vitro development of a taxol release system", *Journal of Controlled Release*, 71(2), (2001), 193-202.

Attawia, Mohamed A., et al., "The Long Term Osteoblast Response to Poly(anhydride-co-imides): A New Degradable Polymer for Use in Bone", *Proceedings of the Fifth World Biomaterials Congress*, Toronto, Canada, (1996), 113.

Beaton, Michael L., et al., "Synthesis of a novel poly(anhydride-ester)", *The Rutgers Scholar—An Electronic Bulletin of Undergraduate Research*, vol. 3, http://ww.scils.rutgers.edu/~weyang/ejournal/volume03/beatuhri/beatuhri.htm, (2001), 1-7.

Bedell, Christi, et al., "Processing and Hydrolytic Degradation of Aromatic, Ortho-Substituted Polyanhydrides", *Journal of Applied Polymer Science*, 80, (2001), 32-38.

Brown, Joseph P., et al., "A Polymeric Drug for Treatment of Inflammatory Bowel Disease", *Journal of Medicinal Chemistry*, 26(9). (1983),1300-1307.

Campo, Cheryl J., et al., "Polyanhydrides: the effects of ring substitution changes on polymer properties", *Polymer Bulletin*, 42, (1999),61-68.

Chafi, N., et al., "Dosage Form with Salicylic Acid Attached to the Polyanhydride Polymer Dispersed in an Eudragit Matrix", *International Journal of Pharmaceutics*, 52, (1989), 203-211.

Chatterjee, Ranjit, et al., "Mechanism for the Increase in Solubility of Deoxyhemoglobin S Due to Cross-Linking the β Chains between Lysine-82$β_1$ and Lysine-82/$β_2$", *Biochemistry*, 21(23), (1982), 5901-5909.

Conix, Andre, "Aromatic Poiyanhydrides, a New Class of High Melting Fiber-Forming Polymers", *Journal of Polymer Science*, XXIX, (1958), 343-353.

Conix, Andre, "New High-Melting Fibre-Forming Polymers", *Die Makromolekulare Chemie*, XXIV, (1957), 76-78.

Conix, Andre, "Poly [1,3-bis (p-carboxyphenoxy)—Propane anhydride)]", *Macromolecular Synthesis*, 2, (1996), 95-99.

Davaran, Soodabeh, et al., "Release of 5-amino Salicylic Acid from Acrylic Type Polymeric Prodrugs Designed for Colon-specific Drug Delivery", *Journal of Controlled Release*, 58(3), (1999), 279-287.

Domb, A. J.,et al., "Polyanhydrides. I. Preparation of High Molecular Weight Polyanhydrides", *Journal of Polymer Science: Part A: Polymer Chemistry*, vol. 25, (1987), pp. 3373-3386.

Domb, Abraham J., "Synthesis and Characterization of Biodegradable Aromatic Anhydride Copolymers", *Macromolecules*, 25, (1992), 12-17.

Dukovic, Gordana, et al., "Novel degradable poly(anhydride-esters) for controlled drug release", The Rutgers Scholar—An Electronic Bulletin of Undergraduate Research, 1, http://www.scils.rutgers.edu/~weyang/ejournal/volume01/uhriduko/uhriduko.htm, (1999),1-10.

Erdmann, Laura, et al., "Chapter 5: Polymeric Prodrugs: Novel Polymers with Bioactive Components", *In: Tailored Polymeric Materials for Controlled Delivery Systems*, I. McCulloch, et al., (Editors), ACS Symposium Series 709, American Chemical Society: Washington, D.C., (1998), 83-91.

Erdmann, Laura, et al., "Degradable poly(anhydride ester) implants: effects of localized salicylic acid release on bone", *Biomaterials*, 21(24), (2000), 2507-2512.

Erdmann, Laura, et al., "Polymer Prodrugs with Phamaceutically Active Degradation Products", *Polymer Preprints*, 38(2), (1997), 570-571.

Erdmann, Laura, et al., "Polymeric Prodrugs: Novel Polymers for Delivery of Salicylic Acid", *Annals of Biomedical Engineering*, 26 (Suppl. 1), Abstract No. PB.26, Annual Fall Meeting, (1998), S-124.

Erdmann, Laura, et al., "Polymeric Salicylic Acid: In Vitro and In Vivo Degradation", *Polymer Preprints*, 39(2), (1998), 224-225.

Erdmann, Laura, et al., "Synthesis and Characterization of a Polymeric Prodrug", *Proceedings of the American Chemical Society Divi-* sion of Polymeric Materials: Science and Engineering, 78, Abstract of Spring Meeting, Dallas, TX,(1998),194.

Erdmann, Laura, et al., "Synthesis and degradation characteristics of salicylic acid-derived poly(anhydrid-esters)", *Biomaterials*, 21(19), (2000),1941-1946.

Giammona, G., et al., "Polymeric Prodrugs alpha beta polyhyroxyethyl-dl-aspartamide as macromolecular carrier for some non-steroidal anti-inflammatory agents", *Abstract from Database BIOSIS Online, Biosciences Information Service*, Philadelphia, PA, Original Publication from the International Journal of Pharmaceutics (Amsterdam), (1989), 1 page.

Gouin, S., et al., "New Polyanhydrides Made from a Bile Acid Dimer and Sebacic Acid: Synthesis, Characterization and Degradation", *Macromolecules*, 33, (2000), 5379-5383.

Heasman, P. A., et al:, "The effect of a topical non-steroidal anti-inflammatory drug on the development of experimental gingivitis in man.", *J Clin Periodontol.*, 16(6), (1989), 353-358.

Heasman, P. A., et al., "The use of topical flurbiprofen as an adjunct to non-surgical management of periodontal disease.", *J Clin Periodontol.*, 20 (6), (1993), 457-464.

Ibim, S., et al., "Controlled Release Based on Poly(anhydride-co-Imides)", *Proc. Intern. Symp. Control. Rel. Bioact. Mater.*, 22, (1995), 2 pgs.

Ibim, S. M., et al., "Poly(anhydride-co-imides): In Vivo Biocompatibility in a rat model", *Biomaterials*, 19(10), (1998), 941-951.

Ibim, S. E., et al., "Preliminary in vivo report on the osteocompatibility of poly(anhydride-co-imides) evaluated in a tibial model.", *Journal of Biomedical Material Research*, 43(4), (1998), 374-379.

Jeffcoat, M. K., et al., "A comparison of topical ketorolac, systemic flurbiprofen, and placebo for the inhibition of bone loss in adult periodontitis", *J Periodontol.*, 66(5), (1995), 329-338.

Jeffcoat, M. K., "The Effect of Systemic Flurbiprofen on Bone Supporting Dental Implants", *Journal American Dental Association*, 126, (1995), 305-311.

Jiang, H. L., et al., "Synthesis, Characterization and In Vitro Degradation of a New Family of Alternate Poly(ester-anhydrides) Based on Aliphatic and Aromatic Diacids", *Biomaterials*, 22(3), (2001), 211-218.

Kornman, K. S., et al., "Effects of topical applications of meclofenamic acid and ibuprofen on bone loss, subgingival microbiota and gingival PMN response in the primate *Macaca fascicularis*", *J Periodontal Res.*, 25(5), (1990), 300-7.

Krogh-Jespersen, E., et al., "Synthesis of a Novel Aromatic Polyanhydride Containing Aminosalicylic Acid", *Polymer Preprints*, 41(1), (2000), 1048-1049.

Langer, Robert, "New Methods of Drug Delivery", *Science*, 249(4976), (1990), 1527-1533.

Laurencin, C. T., et al., "Poly(anhydricles-co-imides): In Vivo Biocompatibility Study", *23rd Annual Meeting of the Society for Biomaterials*, New Orleans, LA, (1997), 483.

Laurencin, C. T., et al., "The Biocompatibility of Poly(anhydride-co-imides): High Strength Polymers for Controlled Drug Delivery", *Proc. 24th Int'l Symp. Control. Rel. Bioact. Mater.*, (1997), 973-974.

Laurencin, C. T., et al., "The Bone Biocompatibility of Poly(anhydride-co-imides)—A new generation degradable Polymer for Orthopedic Applications", *41st Annual Meeting of the Orthopedic Research Society*, Orlando, FL, (1995),143-24.

Laurencin, C. T., et al., "The Controlled Delivery of Radiosensitizers: Taxol Treatment for Ewing Sarcoma", *Proc. of the 25th Int'l Symp. Control. Rel. Bioact. Mater.*, (1998), 236-237.

Lawrence, H. P., et al., "Pharmacokinetic and safety evaluations of ketoprofen gels in subjects with adult periodontitis", *J Dent Res.* 77(11), (1998), 1904-12.

Li, K. L., et al., "The effect of ketoprofen creams on periodontal disease in rhesus monkeys", *J Periodontal Res.* 31(8), (1996), 525-32.

Longer, Mark A., et al., "Sustained-Release Drug Delivery Systems", *Remington's Pharmaceutical Sciences*, 18th Edition, Chapter 91 (1990), 1676-1693.

Macedo, B., et al., "The in Vivo Response to a Bioactive Biodegradable Polymer", *Journal of Dental Research*, 78 Abstract No. 2827, (1999), 459.

Macedo, B., et al., "The In Vivo Response to Bioactive Polyanhydride Monofilament", *Journal of Dental Research*, 79 (Abstract No. 3872), (2000), 627.

March, Jerry, "Advanced organic chemistry : reactions, mechanisms, and structure", *4th Edition New York : Wiley*, (1992), 419-437.

Paquette, D. W., et al., "Enantiospecific inhibition of ligature-induced periodontitis in beagles with topical (S)-ketoprofen", *J Clin Periodontol.*, 24(8), (1997), 521-528.

Pauletto, N., et al., "Nonsteroidal anti-inflammatory agents: potential modifiers of periodontal disease progression", *J Can Dent Assoc.*, 63(11), (1997), 824-829, 832.

Pinther, P., et al., "Synthesis of Polyanhydrides Containing Ester Groups", *Die Makromolekulare Chemie*, Rapid Communications, 11(8), (1990), 403-408.

Schacht, E., et al., "Polymers for Colon Specific Drug Delivery", *Journal of Controlled Release*, 39 (1996), 327-338.

Seidel, J.O., et al., "Erosion of Poly(anydride-co-imides): A Preliminary Mechanistic Study", *J. Appl. Polym. Sci.*, 62(8), (1996), 1277-1283.

Shen, E., et al., "Morphological Characterization of Erodible Polymer Carriers for Drug Release", *Proc. 26th Int'l Symp. Control. Rel. Bioact. Mater.*, (1999), 717-718.

Swinyard, Ewart A., et al., "Pharmaceutical Necessities", In: *Remington's pharmaceutical sciences by Joseph P Remington*: Alfonso R Gennaro, Easton, Pa. : Mack Pub. Co., ; ISBN: 0912734043, (1990), 1286-1329.

Uhrich, K. E., et al., "Chemical Changes during in vivo degradation of poly(anhydride-imide) matrices", *Biomaterials*, 19(22), (1998), 2045-2050.

Uhrich, K. E., et al., "Degradation of poly(anhydride-co-imides): Novel Polymers for Orthopedic Applications", *Mat. Res. Soc. Symp. Proc.*, 394, (1995), 41-46.

Uhrich, K. E., et al., "In Vitro Degradation Characteristics of Poly(anhydride-imides) Containing Pyromellitylimidoalanine", *J. Appl. Polymer Sci., Part A, Polym. Chem.*, 34 (7), (1996), 1261-1269.

Uhrich, K. E., et al., "In Vitro Degradation Characteristics of Poly(anhydride-imides) Containing trimellitylimidoglycine", *J. Appl. Polymer. Sci.*, 63(11), (1997), 1401-1411.

Uhrich, K. E., et al., "Poly(anhydride-ester) Degradation: Mechanical Changes and Correlation to Antibiotic Release", *American Chemical Society, Abstracts of Papers, Part 2*, Abstract No. 121, 221st ACS National Meeting, San Diego, CA,(2001), Abstract 121.

Uhrich, K. E., et al., "Synthesis and Characterization of Degradable poly(anhydride-co-imides)", *Macromolecules*, 28 (7), (1995), 2184-2193.

Uhrich, K. E., et al., "Synthesis and Characterization of poly(anhydride-co-imides): Solution Polycondensation of Biodegradable Polymers Derived from Amino Acids", *Proc. of the American Chemical Society, Division of Polymeric Materials: Science and Engineering*, 70, Spring Meeting, San Diego, CA, (1994), 239-240.

Uhrich, K. E., et al., "Synthesis of Aminosalicylate-based polyanhydride Prodrugs: Esters, Amides, and Azos", *American Chemical Society, Abstracts of Papers, Part 2*, Abstract No. 407, 222nd ACS National Meeting, Chicago, IL,(2001), Abstract 407.

Vogel, R. I., et al., "The effects of a topically-active non-steroidal anti-inflammatory drug on ligature-induced periodontal disease in the squirrel monkey", *J Clin Periodontol.*, 13(2), (1986), 139-44.

Woo, G. L., et al., "Biological Characterization of a Novel Biodegradable Antimicrobial Polymer Synthesized with Fluoroquinolones", *J Biomed Mater Res*, 59(1), (2002), 35-45.

Yagmurlu, at al., "Sulbactam-Cefoperazone Polyhydroxybutyrate-co-Hydroxyvalerate (PHBV) Local Antibiotic Delivery System: In Vivo Effectiveness and Biocompatibity in the Treatment of Implant-Related Experimental Osteomyelitis", *Journal of Biomedical Materials Research*,46, Abstract Only, Obtained from Medline, Accession No. 1999326670, (Sep. 15, 1999), 494-503.

Yazdi, M., "Effects of non-steroidal anti-inflammatory drugs on demineralized bone-induced bone formation", *Journal of Periodontal Research*, 27(1), (Jan. 1992), 28-33.

Erdmann, Laura, et al., "Polymeric Prodrugs: Novel Polymers with Bioactive Components", *ACS Symposium Series*, vol. 709. Conference: Tailored polymeric materials for controlled delivery systems—Symposium, Development form a symposium sponsored by the Division of Polymer Chemistry at the 214th National Meeting of the American Chemical Society, Las Vegas, Nevada, Sep. 7-11, 1997,(1998), 83-91.

Kompella, U. B., et al., "(C) Means to Enhance Penetration: (4) Delivery Systems for Penetration Enhancement of Peptide and Protein Drugs: Design Considerations", *Advanced Drug Delivery Reviews*, 8, abstract only, obtained from http://www.sciencedirect.com/>, (Jan.-Feb. 1992),2 p.

Kompella, U. B., et al., "Delivery Systems for Penetration Enhancement of Peptide and Protein Drugs: Design Considerations", *Advanced Drug Delivery Reviews*, 46, (2001), 115-162.

Woo et al., "Synthesis and characterization of a novel biodegradable antimicrobial polymer", *Biomaterials*, 21, 1235-1246 (2000).

Patent Cooperation Treaty, International Search Report of the International Search Authority, PCT/US00/33378, Feb. 13, 2002, 7 pages.

* cited by examiner

THERAPEUTIC COMPOSITIONS AND METHODS

CROSS-REFERENCE TO RELATED APPLICATIONS

This application is a continuation of U.S. Ser. No. 10/368,288 filed on Feb. 18, 2003 now abandoned, which is a continuation of International Application Number PCT/US2000/033378 filed Dec. 7, 2000 under 35 U.S.C. §111(a) and also a continuation of U.S. patent application Ser. No. 09/732,516 filed Dec. 7, 2000 now U.S. Pat. No. 6,685,928, which applications claim priority to U.S. Provisional Patent Application No. 60/304,190 filed Dec. 7, 1999. These applications are incorporated herein by reference.

FIELD OF THE INVENTION

The present invention relates to the use of anti-inflammatory agents to enhance the regeneration and healing of tissue (e.g. hard tissue and soft tissue).

BACKGROUND OF THE INVENTION

Polymers comprising aromatic or aliphatic anhydrides have been studied extensively over the years for a variety of uses. For example, in the 1930s fibers comprising aliphatic polyanhydrides were prepared for use in the textile industry. In the mid 1950s, aromatic polyanhydrides were prepared with improved film and fiber forming properties. More recently, attempts have been made to synthesize polyanhydrides with greater thermal and hydrolytic stability and sustained drug release properties.

U.S. Pat. Nos. 4,757,128 and 4,997,904 disclose the preparation of polyanhydrides with improved sustained drug release properties from pure, isolated prepolymers of diacids and acetic acid. However, these biocompatible and biodegradable aromatic polyanhydrides have aliphatic bonds resulting in compounds with slow degradation tunes as well as relatively insoluble degradation products unless incorporated into a copolymer containing a more hydrophilic monomer, such as sebacic acid. The aromatic polyanhydrides disclosed in the '128 Patent and the '904 Patent are also insoluble in most organic solvents. A bioerodible controlled release device produced as a homogenous polymeric matrix from polyanhydrides with aliphatic bonds having weight average molecular weights greater than 20,000 and an intrinsic velocity greater than 0.3 dL/g and a biologically active substance is also described in U.S. Pat. No. 4,888,176. Another bioerodible matrix material for controlled delivery of bioactive compounds comprising polyanhydride polymers with a uniform distribution of aliphatic and aromatic residues is disclosed in U.S. Pat. No. 4,857,311.

Biocompatible and biodegradable aromatic polyanhydrides prepared from para-substituted bis-aromatic dicarboxylic acids for use on wound closure devices are disclosed in U.S. Pat. No. 5,264,540. However, these compounds exhibit high melt and glass transition temperatures and decreased solubility, thus making them difficult to process. The disclosed polyanhydrides also comprise radical or aliphatic bonds which cannot be hydrolyzed by water.

Polyanhydride polymeric matrices have also been described for use in orthopedic and dental applications. For example, U.S. Pat. No. 4,886,870 discloses a bioerodible article useful for prosthesis and implantation which comprises a biocompatible, hydrophobic polyanhydride matrix. U.S. Pat. No. 5,902,599 also discloses biodegradable polymer networks for use in a variety of dental and orthopedic applications which are formed by polymerizing anhydride prepolymers.

Biocompatible and biodegradable aromatic polyanhydrides have now been developed with improved degradation, processing and solubility properties, as well as therapeutic utilities. As demonstrated herein, the new aromatic polyanhydrides are particularly useful in enhancing regeneration and healing of tissue. Thus, these new polyanhydrides can be used in a variety of dental and orthopedic applications.

SUMMARY OF THE INVENTION

It has unexpectedly been discovered that the local administration of an anti-inflammatory agent to tissue provides beneficial effects on the healing and growth of the tissue and on proximally located tissues.

Accordingly, the invention provides a method to promote healing of tissue comprising administering an effective amount of an anti-inflammatory agent to or near the tissue.

The invention provides a method to promote healing of hard tissue comprising administering an effective amount of an anti-inflammatory agent to the hard tissue or to soft tissue near the hard tissue.

The invention also provides a method of treating periodontal disease comprising administering an effective amount of an anti-inflammatory agent at the site of the periodontal disease.

The invention also provides a method of treating a bone fracture comprising fixing the fracture with an orthopedic device comprising an anti-inflammatory agent.

The invention also provides a method to enhance regeneration of tissue comprising administering an effective amount of an anti-inflammatory agent to or near the tissue.

The invention also provides a method to enhance regeneration of hard tissue comprising administering an effective amount of an anti-inflammatory agent to the hard tissue or to soft tissue near the hard tissue.

The invention also provides a method to decrease bone resorption at a site in the body of a patient comprising administering an effective amount of an anti-inflammatory agent at or near the site.

The invention also provides a method to promote healing of bone comprising contacting the bone and surrounding soft tissue with an aromatic polyanhydride comprising a repeating unit having the structure:

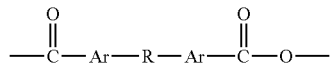

wherein Ar is a substituted or unsubstituted aromatic ring and R is —$Z_1$—$R_1$—$Z_1$— substituted on each Ar ortho to the anhydride group, wherein $R_1$ is a difunctional organic moiety and $Z_1$ is a difunctional moiety selected from the group consisting of esters, amides, urethanes, carbamates and carbonates so that regeneration of bone is enhanced.

The invention also provides a method of treating periodontal diseases in a patient comprising administering to the patient at the site of the periodontal disease an aromatic polyanhydride comprising a repeating unit having the structure:

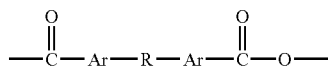

wherein Ar is a substituted or unsubstituted aromatic ring and R is $-Z_1-R_1-Z_1-$ substituted on each Ar ortho to the anhydride group, wherein $R_1$ is a difunctional organic moiety and $Z_1$ is a difunctional moiety selected from the group consisting of esters, amides, urethanes, carbamates and carbonates.

The invention also provides a method of treating bone fractures in a patient comprising fixing the bone fracture with an orthopedic device comprised of or coated with an aromatic polyanhydride comprising a repeating unit having the structure:

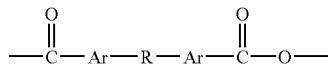

wherein Ar is a substituted or unsubstituted aromatic ring and R is $-Z_1-R_1-Z_1-$ substituted on each Ar ortho to the anhydride group, wherein $R_1$ is a difunctional organic moiety and $Z_1$ is a difunctional moiety selected from the group consisting of esters, amides, urethanes, carbamates and carbonates.

The invention also provides pharmaceutical compositions comprising an anti-inflammatory agent and a pharmaceutically acceptable carrier, which are formulated to provide controlled release of the agent at or near tissue (e.g. hard or soft tissue). Preferably, the compositions are formulated to provide local release of an effective amount of the agent over a period of at least about 2, about 5, about 10, about 20, or about 40 days. The compositions can also preferably be formulated to provide local release of an effective amount of the agent over a period of up to about 3 months, about 6 months, about 1 year, or about 2 years.

The invention also provides the use of an anti-inflammatory agent to prepare a medicament useful for promoting the healing of tissue by administration to or near the tissue.

The invention also provides the use of an anti-inflammatory agent to prepare a medicament useful for decreasing bone resorption at a site in the body of a mammal by administration at or near the site.

The invention also provides the use of an anti-inflammatory agent to prepare a medicament useful to enhance regeneration of tissue by administration to or near the tissue.

The preparation of aromatic polyanhydrides from ortho-substituted bis-aromatic carboxylic acid anhydrides disrupts the crystallinity of the resulting polymer, enhancing solubility and proccessability, as well as degradation properties. The use of hydrolyzable bonds such as esters, amides, urethanes, carbamates and carbonates as opposed to aliphatic bonds in these compounds further enhances these properties.

These aromatic polyanhydrides have a repeating unit within the structure of Formula I:

(I)

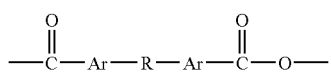

wherein Ar is a substituted or unsubstituted aromatic ring and R is a Bifunctional organic moiety substituted on each Ar ortho to the anhydride group. Ar and R are preferably selected so that the hydrolysis products of the polyanhydrides have a the chemical structure of an anti-inflammatory agent, particularly salicylates such as aspirin, non-steroidal anti-inflammatory compounds, or other aromatic anti-inflammatory compounds. Ar is preferably a phenyl group and R is preferably $-Z_1-R_1-Z_1-$ in which $R_1$, is a difunctional moiety and both $Z_1$s are independently either an ester $-C(=O)O-$, amide $-C(=O)N-$, anhydride $-C(=O)-O-C(=O)-$, carbonate $-O-C(=O)-O-$, urethane $-N-C(=O)-N-$, or sulfide $-S-$ groups. $R_1$ is preferably an alkylene group containing from 1 to 20 carbon atoms, or a group with 2-20 carbon atoms having a structure selected from $(-CH_2-CH_2-O-)_m$, $(CH_2-CH_2-CH_2-O-)_m$ and $(-CH_2-CHCH_3-O-)_m$.

Ortho-substituted bis-aromatic carboxylic acid anhydrides of the present invention are used in the preparation of the aromatic polyanhydrides of the present invention. The ortho-substituted bis-aromatic carboxylic acid anhydrides have the structure of Formula II:

(II)

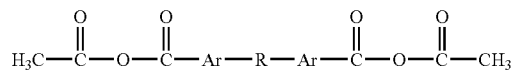

wherein Ar and R, and the preferred species thereof, are the same as described above with respect to Formula I and R is substituted on each Ar ortho to the anhydride group.

The aromatic polyanhydrides of the present invention meet the need for moldable biocompatible biodegradable polymers and are particularly useful in enhancing the healing process of bone and surrounding soft tissue.

Accordingly, the present invention relates to compositions and methods of using compositions comprising a aromatic polyanhydride with a repeating unit of Formula I to enhance healing of tissue (e.g. hard tissue); It has been found that these compositions promote healing in hard tissue by inhibiting inflammation and/or pain in the surrounding soft tissues and by enhancing hard tissue regeneration by promoting growth and/or by reducing bone resorption. To use these compositions to enhance tissue regeneration, it is preferred that the compositions be incorporated into fibers, films, membranes, pastes or microspheres. For this use, it is also preferred that the compositions comprise poly(anhydride esters), referred to herein as bioactive polyanhydrides that degrade into salicylic acid, an anti-inflammatory, antipyretic and analgesic agent. The hard tissue and surrounding soft tissue are directly contacted with the composition so that regeneration and healing is enhanced.

A more complete appreciation of the invention and other intended advantages can be readily obtained by reference to the following detailed description of the preferred embodiments and claims, which disclose the principles of the invention and the best modes which are presently contemplated for carrying them out.

DETAILED DESCRIPTION OF THE INVENTION

Figure 1:
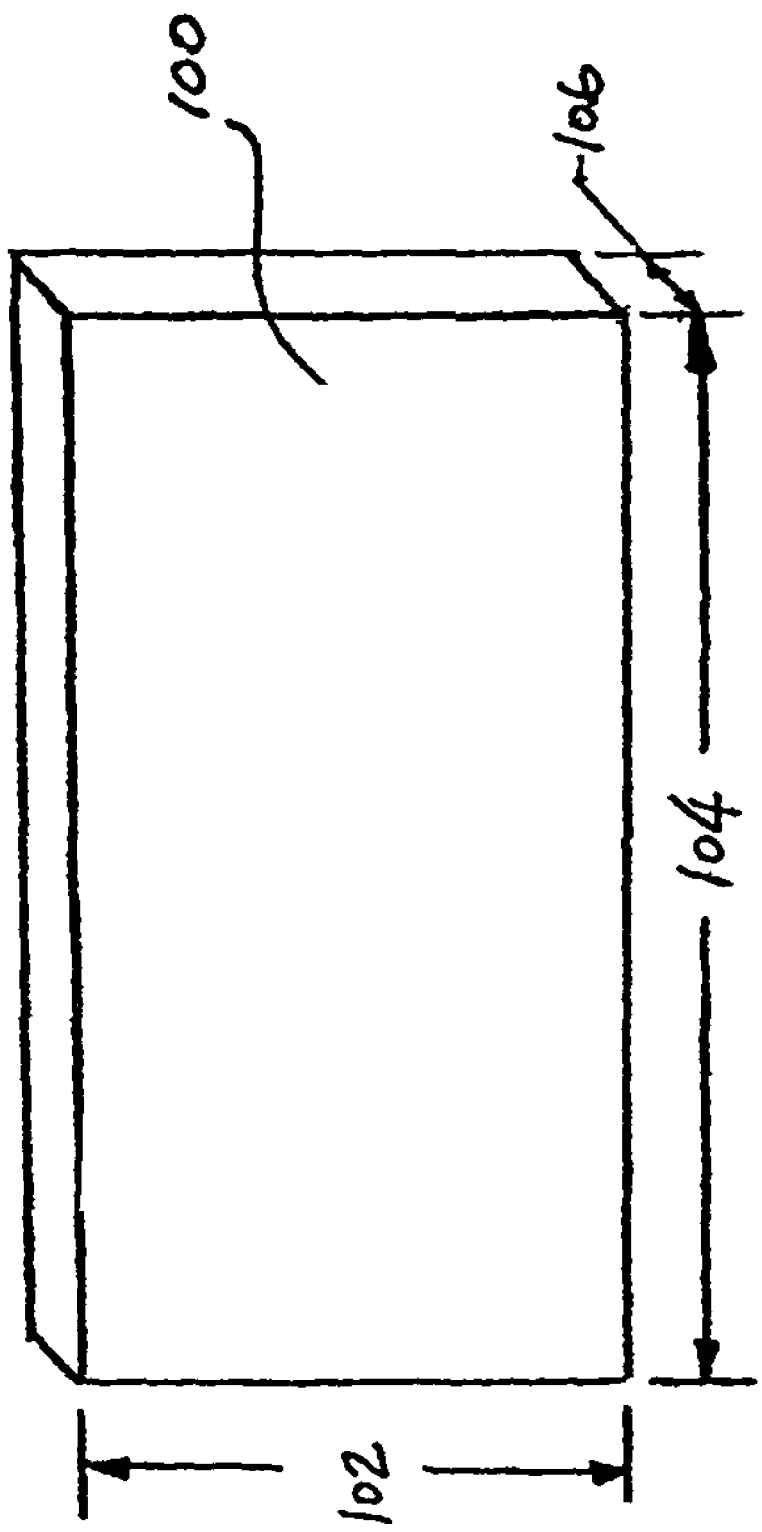
FIG. 1 illustrates a perspective view of a bioactive implant as constructed in accordance with one embodiment.

Applicant has discovered that the local administration of an anti-inflammatory agent on or near bard tissue, such as bone or tooth, enhances the growth and regeneration of the bard tissue and the surrounding soft tissue. Preferably, the anti-inflammatory agent is administered in a form that provides a controlled release of the agent at or near the hard tissue over a period of days or months.

Numerous controlled release mechanisms are known in the art (for example see R. Langer, 1990, *Sciencel*, 249, 1527-1533. Any controlled release mechanism can be used in conjunction with the methods of the invention, provided it allows for the controlled release of the anti-inflammatory agent at or near the site of the tissue. One preferred method for providing the controlled release of an anti-inflammatory agent is to incorporate the agent into a polymer (e.g. a biodegradable polymer). The agent can be dispersed through the polymer matrix, can be appended to the backbone of the polymer, or can be incorporated dizzy into a biodegradable polymer backbone. Typically, any anti-inflammatory agent can be dispersed through a polymer matrix to provide a suitable controlled release formulation. However, the ability of an agent to be appended to or incorporated into a polymer may depend on the functional groups present in the agent. Preferred anti-inflammatory agents that can be appended to or incorporated into a polymer to provide a suitable controlled release formulation are described in greater detail below.

Anti-Inflammatory Agent

Anti-Inflammatory agents are a well known class of pharmaceutical agents which reduce inflammation by acting on body mechanisms (Stedman's Medical Dictionary 26 e., Williams and Wilkins, (1995); Physicians Desk Reference 51 ed, Medical Economics, (1997)).

Anti-inflammatory agents useful in the methods of the invention include Non-steroidal Anti-Inflammatory Agents (NSAIDS). NSAIDS typically inhibit the body's ability to synthesize prostaglandins. Prostaglandins are a family of hormone-like chemicals, some of which are made in response to cell injury. Specific NSAIDS approved for administration to humans include naproxen sodium, diclofenac, sulindac, oxaprozin, diflunisal, aspirin, piroxicam, indomethocin, etodolac, ibuprofen, fenoprofen, ketoprofen, mefenamic acid, nabumetone, tolmetin sodium, and ketorolac tromethamine.

Other anti-inflammatory agents useful in the methods of the invention include salicylates, such as, for example, salicilic acid, acetyl salicylic acid, choline salicylate, magnesium salicylate, sodium salicylate, olsalazine, and salsa late.

Other anti-inflammatory agents useful in the methods of the invention include cyclooxygenase (COX) inhibitors. COX catalyzes the conversion of arachidonate to prostaglandin H2 (PGH2); a COX inhibitor inhibits this reaction. COX is also known as prostaglandin H synthase, or PGH synthase. Two Cox genes, Cox-1 and Cox-2 have been isolated in several species. COX-2 is tightly regulated in most tissues and usually only induced in abnormal conditions, such as inflammation, rheumatic and osteo-arthritis, kidney disease and osteoporosis. COX-1 is believed to be constitutively expressed so as to maintain platelet and kidney function and inter homeostasis. Typical COX inhibitors useful in the methods of the invention include etodolac, celebrex, meloxicam, piroxicam, nimesulide, nabumetone, and rofecoxib.

Preferred anti-inflammatory agents that can be incorporated into a polymer matrix for administration in the methods of the invention include: Isonixin, Amtolmetin Guacil, Proglumetacin, Piketoprofen, Difenamizole, Epirizole, Apazone, Feprazone, Morazone, Phenylbutazone, Pipebuzone, Propyphenazone, Ramifenazone, Thiazolinobutazone, Aspirin, Benoiylate, Calcium Acetylsalicylate, Etersalate, Imidazole Salicylate, Lysine Acetyisalicylate, Morpholine Salicylate, 1-Naphthyl Salicylate, Phenyl Acetysalicylate, Ampiroxicam, Droxicam, S-Adenosylmethionine, Amixetine, Benzydamine, Bucolome, Difenpiramide, Emorfazone, Guaiazulene, Nabunetone, Nimesulide, Proquazone, Superoxide Dismutase, and Tenidap.

Preferred anti-inflammatory agents that can be appended to a polymer for administration in the methods of the invention include: Etofenamate, Talniflumate Terofenamate, Acemetacin, Alclofenac, Bufexamac, Cinmetacin, Clopirac, Felbinac, Penclozic Acid, Fentiazac, Ibufenac, Indomethacin, Isofezolac, Isoxepac, Lonazolac, Metiazinic Acid, Mofezolac, Oxametacine, Pirazolac, Sulindac, Tiaramide, Tolmetin, Tropesin, Zomepirac, Bumadizon, Butibufen, Fenbufen, Xenbucin Clidanac, Ketorolac, Tinoridine, Benoxaprofen, Bermoprofen, Bucloxic Acid, Fenoprofen, Flunoxaprofen, Flurbiprofen, Tbuprofen, Tbuproxam, Indoprofen, Ketoprofen, Loxoprofen, Naproxen, Oxaprozin, Pirprofen, Pranoprofen, Prodznic Acid, Suprofen, Tiaprofenic Acid, Zaltoprofen, Benzpiperylon, Mofebutazone, Oxyphenbutazone, Suxibuzone, Acetaminosalol, Parsalmide, Phenyl Salicylate, Salacetamide, Salicylsulfuric Acid, Isoxican, Lomoxicam, Piroxicam, Tenoxicam, ε-Acetamidocaproic Acid, Bendazac, α-Bisabolol, Paranyline, Perisoxal, and Zileuton.

Preferred anti-inflammatory agents that can be incorporated into a polymer backbone for administration in the methods of the invention include: Enfenamic Acid, Aceclofenac, Glucametacin, Alminoprofen, Caiprofen, Xinoprofen, Salsalate, 3-Amino-4-hydroxybutyric Acid, Ditazol, Fepradinol, and Oxaceprol.

Preferred anti-inflammatory agents that posses suitable ortho functionality to be incorporated into the backbone of a polymer of formula (I) as described herein include: Flufenamic Acid, Meclofenamic Acid, Mefenamic Acid, Niflumic Acid, Tolfenamic Acid, Amfenac, Bromfenac, Diclofenac Sodium, Etodolac, Bromosaligenin, Diflunisal, Fendosal, Getitisic Acid, Glycol Salicylate, Salicilic Acid, Mesalamine, Olsalazine, Salicylamide O-Acetic Acid, Sulfasalazine, For any anti-inflammatory agent referred to herein by a trade name it is to be understood that either the trade name product or the active ingredient possessing anti-inflammatory activity from the product can be used. Additionally, preferred agents identified herein for incorporation into a polymer backbone can also preferably be appended to a polymer or can be incorporated into a polymer matrix. Preferred agents that can be appended to a polymer can also preferably be incorporated into a polymer matrix.

Definitions

As used herein the term "hard tissue" includes tissue that has become mineralized, such as, for example, bone, cartilage, and tooth.

As used herein, administering an agent "to or near the tissue" means administering the agent so that it is in direct contact with the tissue or administering the agent to a location proximal to tissue, so that the agent can produce hew desired or stated therapeutic effect.

As used herein, "administering an anti-inflammatory agent to bard tissue" means applying the agent so that it is in direct contact with the bard tissue.

As used herein, "administering an anti-inflammatory agent to the soft tissue near hard tissue" means applying the agent to the soft tissue proximal to the hard tissue, so that the agent can produce the desired or stated therapeutic effect.

As used herein the term, "formulated for controlled release" means that the agent is formulated such that it will be released over an extended period of time when administered according to the methods of the invention. For example, the agent can conveniently be formulated so that it will be released over a period of at least about 2, about 5, about 10, about 20, or about 40 days. Preferably, the agent is formulated so that it is released over at least about 5 or about 10 days. The agent can also preferably be formulated so that it is released over a period of about 30 to about 90 days. For the treatment of hard tissue, the agent is preferably formulated so that it is released over a period of about 30 to about 90 days. For the treatment of soft tissue, the agent is preferably formulated so that it is released over a period of about 1 to about 30 days, more preferably about 2 to about 25 days.

As used herein, an agent is "appended" to a polymer when the agent is bonded to the polymer as a side chain or side group, but is not part of the polymer backbone. Preferably, the agent is bonded to the polymer through a linkage that is suitable to release the agent when the polymer is administered according to the methods of the invention. For example, the agent can conveniently be linked to a polymer through a hydrolyzable linkage such as an anhydride or ester linkage.

As used herein, the term "dispersed through the polymer matrix" means that an anti-inflammatory agent is located within the matrix of a polymer such that it can be released in a controlled fashion within the body. Preferably, the polymer matrix comprises a biodegradable polymer.

As used herein, the term "at the site of the periodontal disease" means at a site that is at or proximal to the site of the periodontal disease, such that when an agent is administered to the site, the agent can produce a beneficial effect and ameliorate one or more symptoms of the periodontal disease.

As used herein, the term "gingival cleft" means the space between the soft tissue of the gum and the tooth.

As used herein, the term "fixing the fracture" means to hold the fractured pieces together or to stabilize the fracture.

As used herein; the term "enhance regeneration of hard tissue" means to allow or to facilitate the growth of the hard tissue in abnormal manner.

As used herein, "administering an anti-inflammatory agent at the site" means applying the agent so that it is in direct contact with the site.

As used herein, "administering an anti-inflammatory agent near the site" means applying the agent proximal to the site, so that the agent can produce the desired or stated therapeutic effect (e.g. reduce bone resorption at the site).

As used herein, the term "periodontal disease" includes any abnormality, either inflammatory or degenerative, of the tissue around the tooth.

As used herein, the term "healing" means the restoration to normal health.

Aromatic polyanhydrides with improved degradation properties and processability have now been developed These compounds have repeating units with the structure of Formula I:

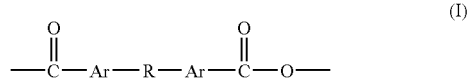
(I)

wherein Ar is a substituted or unsubstituted aromatic ring and R is a difunctional organic moiety substituted on each Ar ortho to the anhydride group. Ar and R are preferably selected so that the hydrolysis products of the polyanhydrides have a chemical structure resembling pharmaceutically-active materials, particularly salicylates such as aspirin, non-steroidal anti-inflammatory naphthyl or phenyl propionates such as ibuprofen, ketoprofen, naproxen, and the like, or other aromatic anti-inflammatory compounds such as indomethacin, indoprofen, and the like. In particular, Ar is preferably a phenyl group and R is preferably —$Z_1$—$R_1$—$Z_1$— in which $R_1$, is a difunctional moiety and both $Z_1$s are independently either an ester, amide, anhydride, carbonate, urethane or sulfide groups. $R_1$ is preferably an alkylene group containing from 1 to 20 carbon atoms, or a group with 2-20 carbon atoms having a structure selected from (—$CH_2$—$CH_2$—O—)$_m$, (—$CH_2$—$CH_2$—$CH_2$—O—)$_m$ and (—$CH_2$—$CHCH_3$—O—)$_m$ or $R_1$ may have the structure —$R_2$—$Z_2$—$R_3$-1 wherein $R_2$ and $R_3$ are independently alkylene groups containing from 1 to 19 carbon atoms or groups having from 2 to 18 carbon atoms having a structure selected from (—$CH_2$—$CH_2$—O—)$_m$, (—$CH_2$—$CH_2$—$CH_2$—O—)$_m$, and (—$CH_2$—$CHCH_3$—O—)$_m$, and $Z_2$ is selected from the difunctional moieties described above with respect to $Z_1$.

Ar may be an alkylaryl group, in which a difunctional organic moiety is positioned between each anhydride carbonyl group and the corroding aromatic ring. Preferably, however, each carbonyl group is directly substituted on the corresponding aromatic ring.

Preferred polymers of the present invention have repeating units with the structure of Formula I in which Ar is a phenyl ring and R is selected from —$Z_1$—(—$CH_2$)$_n$—$Z_1$, —$Z_1$(—$CH_2$—$CH_2$—O—)$_m$—$Z_1$, —$Z_1$(—$CH_2$—$CH_2$—$CH_2$—O—)$_m$—$Z_1$, and —$Z_1$(—$CH_2$—$CH_2$—$CH_2$—$CH_2$—O—)$_m$—$Z_1$—, and —$Z_1$(—$CH_2$—$CHCH_3$—O—)$_m$-$Z_1$-, wherein $Z_1$ is an ester or amide group and n is from 1 to 20 inclusive, and preferably is 6, and m is selected so that R has from 2 to 20, and preferably 6, carbon atoms.

A preferred polymer useful in the methods of the invention is a polymer of Formula I:

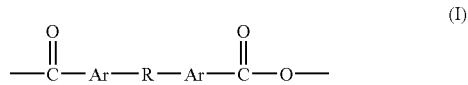
(I)

wherein Ar is a substituted or unsubstituted aromatic ring and R is a difunctional organic moiety. R is preferably —$Z_1$—$R_1$—$Z_1$— in which $R_1$, is a difunctional moiety and each $Z_1$ is independently an ester —C(=O)O—, amide —C(=O)N—, anhydride —C(=O)—O—C(=O)—, carbonate —O—C(=O)—O—, urethane —N—C(=O)—N—, or thioester —C(=O)S—. $R_1$ is preferably an alkylene group containing from 1 to 20 carbon atoms.

The aromatic polyanhydrides of the present invention may be p by the method described in Conix, Macromol. Synth., 2, 95-99 (1996), in which dicarboxylic acids are acetylated in an excess of acetic anhydride followed by melt condensation of the resulting carboxylic acid anhydride at 180° C. for 2-3 hours. The resulting polymers are isolated by precipitation into diethyl ether from methylene chloride. The described process is essentially the conventional method for polymerizing bis-aromatic dicarboxylic acid anhydrides into aromatic polyanhydrides.

Aromatic polyanhydrides in accordance with the present invention have average molecular weights of about 1500 daltons, up to about 50,000 daltons, calculated by Gel Permeation Chromatography (GPC) relative to narrow molecular weight polystyrene standards. Preferred aromatic polyanhydrides have average molecular weights of about 1500 daltons, up to about 35,000 daltons.

The aromatic polyanhydrides of the present invention are produced from ortho-substituted bis-aromatic carboxylic acid anhydrides having the structure of Formula II:

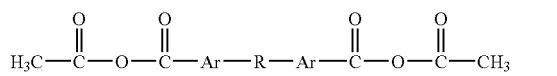
(II)

in which Ar, R and the preferred species thereof are the same as described above with respect to Formula I. As noted above, ortho-substituted bis-aromatic cazboxylic acid anhydrides are prepared by acetylation of the corresponding ortho-substituted bis-aromatic carboxylic acids in an excess of acetic anhydride. The dicarboxylic acids have the structure of Formula III

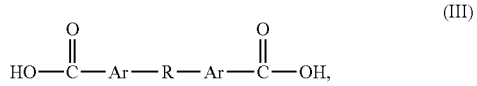
(III)

wherein Ar, R and the preferred species thereof are the same as described above with respect to Formula I.

The dicarboxylic acids are prepared by reacting a stoichiometric ratio of aromatic carboxylic acid having the structure $Z_3$—Ar—COOH and a compound having a structure $Z_4$—R—$Z_4$ wherein Ar is a substituted or unsubstituted aromatic ring on which $Z_3$ is substituted ortho to the carboxylic acid group, R is a difunctional organic moiety and $Z_3$ and $Z_4$ are functional groups selected to provide the linkage desired between the difunctional organic moiety and the two aromatic rings.

Suitable $Z_3$ and $Z_4$ functional groups, and the manner in which they may be reacted to produce the bis-aromatic dicarboxylic acids of the present invention, may be readily determined by those of ordinary skill in the art without undue experimentation. For example, for aromatic polyanhydrides having the structure of Formula I in which Ar is a phenyl group and R is —O—(—$CH_2$—)$_6$—O—, the ortho-substituted bisaromatic dicarboxylic acid starting material may be prepared by reacting o-salicylic acid with 1,6-dibromohexane. For aromatic polyanhydrides having the structure of Formula I in which Ar is a phenyl group and R is —O—C(=O)—($CH_2$—)$_6$—C(=O)—O—, the ortho-substituted bisaromatic dicarboxylic acid starting material may be prepared by reacting o-salicylic acid with 1,6-dioctanoic acid.

The aromatic polyanhydrides used in the present invention can be isolated by known methods commonly employed in the field of synthetic polymers to produce a variety of useful articles with valuable physical and chemical properties. The new polymers can be readily processed into pastes, and gels or solvent cast to yield films, membranes, coatings, microspheres, chips and fibers with different geometric shapes for design of various medical implants, and may also be processed by compression molding and extrusion. Medical implant applications include the use of aromatic polyanhydrides to form shaped articles such as vascular grafts and stents, bone plates, sutures, implantable sensors, implantable drug delivery devices, stents for tissue regeneration, scaffolding for supporting new cell growth and other articles that decompose harmlessly within a known time period. For the present invention, it is preferred that the polyanhydride be incorporated into films, membranes, pastes, gels, microspheres, chips or fibers useful in dental and orthopedic applications.

It has now been demonstrated that tie polymers comprising these aromatic polyanhydrides having a repeating unit with the structure of Formula I in which Ar and R are selected to provide aromatic polyanhydrides that hydrolyze to form therapeutically useful salicylates are particularly useful in enhancing regeneration of tissue. Examples of the therapeutically useful salicylates include, but are not limited to, thymotic acid, 4,4-sulfinyldinailine, 4-sulfanilamidosalicylic acid, sulfanilic acid, sulfanilylbenzylamine, sulfaloxic acid, succisulfone, salicylsulunic acid, salsallate, salicylic alcohol, salicilic acid, orthocaine, mesalamine, gentisic acid, enfenamic acid, cresotic acid, aminosalicylic acid, aminophenylacetic acid, acetylsalicylic acid, and the like. The identification of Ar and R moieties that provide aromatic polyanhydrides that hydrolyze to form such therapeutically useful salicylates can be readily determined by those of ordinary skill in the art without undue experimentation.

A preferred salicylate for incorporation into the polymers of formula (I) is salicylic acid, thymotic acid, 4-sulfanilamidosalicylic acid, mesalamine, gentisic acid, enfenamic acid, cresotic acid, or aminosalicylic acid.

The quantity of aromatic polyanhydride that hydrolyzes to form an amount of therapeutic salicylate effective to relieve inflammation and promote healing of bone can be readily determined by those of ordinary skill in the art without undue experimentation. The quantity essentially corresponds stoichiometrically to the amount of salicylate known to produce an effective treatment. Oral dosage forms of aromatic polyanhydrides that hydrolyze to form other therapeutic non-steroidal anti-inflammatory compounds and other therapeutic compounds are prepared and administered in a similar manner.

Most degradable or absorbable devices for dental or orthopedic applications cause local inflammation. In the present invention, however, use of compositions such as films, membranes, fibers, pastes, gels and microspheres comprising an aromatic polyanhydride that hydrolyzes to form a therapeutically useful salicylate in dental and orthopedic applications actually deceases local inflammation and/or pain. These compositions can also be incorporated into matrices to provide preformed or adaptable scaffolding for cell in growth. Further, it has been found that use of these compositions promotes the healing process of the tissue (e.g. bone) through enhanced regeneration of these tissues. Selection of the form of the composition to be used is preformed routinely by those of skill in the art based upon the type of injury and the tissue healing to be promoted.

Compositions comprising an aromatic polyanhydride can be used to coat orthopedic devices for fixation of bone fractures such as pins or screws, thereby decreasing the local inflammation and bone resorption associated with these devices. Films comprising an aromatic polyanhydride are also believed to be useful as orthopedic devices to enhance the healing process of bone fractures.

Fibers useful as suture materials can also be comprised of the aromatic polyanhydride. For example, polymer fibers are used frequently in oral surgery to suture cleft palates. Use of an aromatic polyanhydride which degrades to a therapeutic salicylate would enhance the regeneration of the tissue via the sutures while decreasing the pain and inflammation associated with the surgery via the degradation products.

Films, membranes, pastes, gels, chips and microspheres comprising the aromatic polyanhydrides can also be used to decease dental pain and promote healing within a tooth, in the pulp chamber and root canal.

Films or membranes comprising the aromatic polyanhydrides can also be used in guided bone or tissue regeneration. Following surgery, especially oral or dental surgery, proper healing of the wound requires both bone and soft tissue regeneration. It is well known, however, that bone heals more slowly than the surrounding tissues such as the gums. In fact, oftentimes in growth of other tissues into an area prevents the required regeneration of the bone. For example, removal of a substantial portion of the tooth root due to resorption or disease leaves a cavity which is oftentimes quickly filled by connective tissue. This in growth of connective tissue effectively prevents bone regeneration.

Accordingly, a procedure refereed to as guided bone or tissue regeneration has been developed to overcome this difficulty. In this method, a membrane is surgically inserted around the periphery of the wound cavity. The membrane prevents or inhibits the invasion of the wound cavity by unwanted cells types and allows the preferred cells to grow into the cavity, thereby healing the wound. This procedure is also used to regenerate bone around teeth and on edentulous jaw ridges in association with implant reconstruction.

Two membranes commonly used in guided tissue regeneration include a synthetic, non-resorbable-polytetrafluoroethylene membrane such as GORETEX and synthetic membranes formed from glycolide and lactide copolymers. U.S. Pat. No. 5,837,278 also describes a resorbable collagen membrane for use in guided tissue regeneration. It is believed that films comprising aromatic polyanhydrides would also be useful in this procedure.

Compositions comprising an aromatic polyanhydride that hydrolyzes to form a therapeutically useful salicylate are believed to be particularly useful in treatment of periodontal diseases. Periodontal diseases, including a group of related microbial-induced chronic inflammatory disorders and a disorder referred to periodontal dehiscence, destroy the tissue supporting the teeth. These diseases can result in loss of normal soft and hard tissue architectures at sites adjacent to the affected teeth. Incorporation of these compositions into films, membranes, pastes, fibers or microspheres for use in treatment of periodontal disease is expected to accelerate the recovery/restoration of new healthy periodontal architecture while reducing post-operative pain after periodontal surgery. Further, the lower pH environment which results from degradation into salicylates is unfavorable to growth of some periodontic bacteria Thus, use of these compositions is also expected to decrease infections in periodontal procedures.

In vivo studies were conducted to compare the affects of a polymer system of the present invention (referred to herein as the bioactive polymer or implant) and a chemically similar polyanhydride system (referred to herein as the control polyanhydride) on the healing process. The sole chemical difference between these two systems is the replacement of the ether bond in the polyanhydride of the bioactive polymer with an ester bond thereby resulting in degradation to salicylic acid as compared to a non-active component in the control polyanhydride. In these experiments, the polymers were compression-molded into films with thicknesses of 0.1, 0.2 and 0.3 mm and cut into 0.5 mm wide strips.

In these experiments, mice (n=10) were anesthetized and the palatal gingival mucosa adjacent to the maxillary first molar was reflected to expose the palatal and alveolar bone. A polymer film was then placed on the bone adjacent to the tooth. The tissue was repositioned and the procedure was repeated on the contra lateral side. Polymer films were randomly placed (left vs. right) with each mouse carrying both polymers. Mice were fed a ground diet and water ad libitum and weighed weekly. Mice were sacrificed at 1, 4 and 20 days post surgical insertion.

Visual intraoral examination of the mucosa covering the implantation sites was performed with a dissecting microscope under optimum lighting. Magnification was varied from 5 to 40 times normal size. Photographs were taken to record the morphological changes observed.

Polymer membranes of thicknesses 0.1 and 0.2 mm were not visible under the microscope at 4 and 20 days post insertion. However, thicker membranes (0.3 mm) were still observable after 20 days. For the control polyanhydride films, the mucosa was red and thin near the implant with the surrounding tissue inflamed at days 1 and 4. By day 14, the tissue was slightly puffy in tree animals while the tissue was within normal limits for the remaining 5 animals. In contrast, the tissue surrounding the bioactive polymer implants was slight puffy after day 1 but within normal limits in all animals by day 4. Further, considerable swelling was observed on the side bearing the control polyanhydride, was the side with the bioactive polymer showed a progressively normal mucosa. The tissue surrounding the control polyanhydride was very swollen and white, whereas the tissue adjacent to the bioactive implant was less swollen and normal in color. The three maxillary molar palatal ridges (anterior, middle and posterior) were clearly visible. However, the anterior and middle ridges coalesced because of the swelling and blanching on the control polyanhydride side. This effect was most pronounced at day 13. By days 15 and 20, blanching and swelling on the control polyanhydride side were considerably diminished.

Histological examination of tissues from the mice was also performed. After sacrifice, tissues were fixed in 10% formalin, decalcified, embedded in paraffin, sectioned serially at 4 μm thickness, and stained with hematoxylin and eosin. The sections were subjected to microscopic evaluation and histometric assessment using 4, 10 and 20× magnifications. The histopathological examination correlated well with visual observations.

One mouse was scarified 24 hours post implantation. The histology showed heavy infiltration of polymorphonuclear (PMN) leucocytes and erythrocytes. The 0.1 mm films were mostly dissolved during the tissue processing procedure. The bone was denuded from the periosteum and the polymer was in direct contact. The gingival epithelium and connective tissue below the subcular epithelium was broken. The coronal part of the periodontal ligament linking the alveolar bone to the coronal cementum was mostly intact. The method for reflecting the palatal mucosa was effective in not damaging the periodontal ligament below the level of the bone and coronal cementum. There was no significant difference between the bioactive and control side except for the decease in swelling on the bioactive side.

Two mice were sacrificed four days post implantation. At this time point, some polymeric material remained in all sites. The 0.1 mm film was in direct contact with the palatal bone. An extensive, thin layer of palatal epithelium was observed that surrounded portions of the polymer specimens. The extent of the epithelium along the membranes was greater for the bioactive than for the control polyanhydride site. Similarly, the PMN cells inflammatory infiltrate was greater on the control polyanhydride side than on the bioactive polymer side. The infiltrate was denser below the epithelium adjacent to the membrane. The infiltrate along the palatal bone was much less.

Six mice were sacrificed at twenty days post implantation. At this time point, small remnants of a 0.3 mm film in only one specimen were present; all other specimens were devoid of polymer. Gingival epithelium including subcular and junctional were essentially restored on all sites. Two specimens showed external resorption that involved cementum and dentin on the controll polyanhydride side. Tissue specimens with bioactive polymer showed no alveolar bone, cementum and dentin resorption. However, a significant amount of new bone could be observed coronal to the reversal lines in the sites bearing bioactive films. New bone was also found in the control polyanhydride sites, but at insignificant amounts as compared to the bioactive polymer side. Inflammatory cell infiltrate was present and consisted primarily of PMN cells and macrophages. No erythrocytes were observed except within the vasculature. The intensity of the infiltrate was lower on the bioactive polymer sites.

Quantitative analyses were also performed via electronic images taken of the tissue sections using a Kodak MDS-120 camera attached to an Olympus CH-triocular microscope at magnifications of 4×, 10× and 40×. Using NIH Images 1.61 software, the area of bone, connective tissue, epithelium and artifacts at the lowest magnification were determined. Perpendicular to the widest part of the tooth, a square box was drawn with sides 575 pixels in length. The areas of bone, connective tissue, epithelium and artifacts were determined by the number of pixels within -the defined box. All images were blindly analyzed. Sections were taken from mice sacrificed after 20 days from membranes that were either 0.3 or 2 mm thick. Results are shown in the following Table.

| Polymer | Bone Area (0.3 mm) | Bone Area (0.2 mm) |
| --- | --- | --- |
| Control Polyanhydride | 94,750 | 85,563 |
| Bioactive Polymer | 129,637 | 99,702 |

These experiments demonstrate that implantation of a film comprising an aromatic polyanhydride that hydrolyzes to form a therapeutically useful salicylate resulted in less swelling in tissues adjacent to the film and a decrease in the density of inflammatory cells as compared to other polyanhydride films. Further, little or no bone resorption was observed in the regions near the film as indicated by increased thickness of the palatal. In fact, data from quantitative analyses are indicative of compositions used in the present invention either promoting bone growth or decreasing bone resorption relative to the polyanhydride composition Accordingly, use of compositions comprising an aromatic polyanhydride that hydrolyzes to form a therapeutically useful salicylate in dental and osteopathic applications enhances the healing process of bone as compared to other polymer systems routinely used in these applications.

The invention also provides for bioactive implants which are useful for treating periodontal disease. As shown in FIG. 1, a bioactive implant 100 comprises a film of material which is sized and shaped to be received in or near the gingival cleft. For instance, the film has a height 102 of about 1-2 mm, a width 104 of about 1-5 mm, and a thickness 106 of about 0.1-2.0 mm It should be noted, however, that other suitably sized films may be configurable to be received in or near the gingival cleft. Other examples for the bioactive implant 100 include, but are note limited to membranes, pastes, gels, chips, or microspheres. The bioactive agent further includes an anti-inflammatory agent, for instance, any of the agents discussed above. Options for the anti-inflammatory agent include, but are not limited to, coatings, agents molded in or with a polymer matrix, or agents embedded in a polymer.

The following non-limiting examples set forth hereinbelow illustrate certain aspects of the invention. All parts and percentages are by weight unless otherwise noted and all temperatures are in degrees Celsius. Except for acetic anhydride and ethyl ether (Fisher Scientific), all solvents and reagents were obtained from Aldrich Chemical. All solvents were HPLC grade. All other reagents were of analytical grade and were purified by distillation or recrystallization.

All compounds were character by a proton nuclear magnetic resonance (NMR) spectroscopy, infrared (R) spectroscopy, gel permeation chromatography (GPC), high performance liquid chromatography (HPLC), differential scanning calorimetry (DSC), and thermal gravimetric analysis (TGA). Infrared spectroscopy was performed on an ATI Mattson Genesis (M100) FTIR Spectrophotometer. Samples were prepared by solvent casting on NaCl plates. $^1$H and $^{13}$C NMR spectroscopy was obtained on a Varian 200 MHZ or Varian 400 MHZ spectrometer in solutions of $CDCl_3$ or $DMSO-d_6$ with solvent as the internal reference.

GPC was performed on a Perkin-Elmer Advanced LC Sample Processor (ISS 200) with PE Series 200 LC pump and a PE Series LC Refractive Index Detector to determine molecular weight and polydispersity. The data analysis was carried out using Turbochrom 4 software on a DEC Celebris 466 computer. Samples were dissolved in tetrahydrofuran and eluted through a mixed bed column (PE PL gel, 5 μm mixed bed) at a flow rate of 0.5 mL/minute. Samples (about 5 mg/mL) were dissolved into the tetrahydrofuran and filtered using 0.5 μm PTFE syringe filters prior to column injection. Molecular weights were determined relative to narrow molecular weight polystyrene standards (Polysciences, Inc.).

Thermal analysis was performed on a Perkin-Elmer system consisting of a TGA 7 thermal gravimetric analyzer equipped with PE AD-4 autobalance and Pyris 1 DSC analyzer. Pyris software was used to carry out data analysis on a DEC Venturis 5100 computer. For DSC, an average sample weight of 5-10 mg was heated at 10° C./minute at a 30 psi flow of $N_2$. For TGA, an average sample weight of 10 mg was heated at 20° C./minute under a 8 psi flow of $N_2$. Sessile drop contact angle measurements were obtained with an NRL Goniometer (Rame-hart) using distilled water. Solutions of polymer in methylene chloride (10% wt/volume) were spun-coated onto glass slips, at 5,000 rpm for 30 seconds.

EXAMPLES

Example 1

Preparation of 1,6-Bis(o-Carboxyphenoxy)Hexane Dicarboxylic Acid

To a mixture of salicylic acid (77.12 g, 0.5580 mole) and distilled water (84 mL) sodium hydroxide (44.71 g, 1.120 mole) was added. The reaction was brought to reflux temperature before 1,6-dibromohexane (45.21 g, 0.2790 mole) was added dropwise. Reflux was continued for 23 hours after which additional sodium hydroxide (11.17 g, 0.2790 mole) was added. The mixture was refluxed for 16 more hours, cooled, filtered, and washed with methanol. The yield was 48.8%.

Example 2

Preparation of 1,6-Bis(o-Carboxyphenoxy)Hexane Monomer (o-CPH)

The dicarboxylic acid of Example 1 was acetylated in an excess of acidic anhydride at reflux temperature. The resulting monomer was precipitated with methylene chloride into an excess of diethyl ether. The yield was 66.8%.

Example 3

Preparation of Poly(1,6-Bis(o-Carboxyphenoxy) Hexane)(Poly(o-CPH))

The monomer of Example 2 was polymerized in a melt condensation performed at 180° C. for 3 hours under vacuum in a reaction vessel with a side arm. The polymerization vessel was flushed with nitrogen at frequent intervals. The polymer was isolated by precipitation into diethyl ether from methylene chloride. The yield was quantitative.

All compounds were characterized by nuclear magnetic resonance spectroscopy, GPC, differential scanning calorimetry (DSC), thermal gravimetric analysis, contact angle measurements, UV spectroscopy, mass spectroscopy, elemental analysis and high pressure liquid chromatography (HPLC).

The o-CPH monomer was polymerized by melt polycondensation for 60 minutes at temperatures ranging from 100° C. to 300° C. Analysis of the resulting polymers by GPC indicated that the highest molecular weight, coupled with the lowest polydispersity index occurred at 260° C.

The poly(o-CPH) was generally soluble in methylene chloride and chloroform, while the poly(p-CPH) was not The poly(o-CPH) was slightly soluble in tetrahydrofuran, acetone and ethyl acetate.

Disks of poly(o-CPH), poly(p-CPH) and, as a reference, poly(lactic acid glycolic acid) were prepared and placed in 0.1 phosphate buffer solution at 37° C. for 4 weeks. The degradation media was replaced periodically. The degradation profile was linear up to three weeks time. In prior art polyanhydride systems, the aromatic groups are para-substituted. This substitution pattern results in higher melt and glass transition temperatures and decreased solubility, thus ultimately making these parasubstituted polymers difficult to process.

Poly(o-CPH), unlike poly(p-CPH), has both a lower melting point (65° C. vs. 143° C.) and glass transition temperature (35° C. vs. 47° C.). It is also possible to solution cast poly(o-CPH) using low-boiling solvents whereas poly(p-CPH) is relatively insoluble in most organic and aqueous solvents. This structural modification gives a polymer whose hydrolysis products are chemically similar to aspirin. Aspirin is an anti-inflammatory agent derived from salicylic acid, which is one of the reagents used to synthesize the inventive polyanhydrides. Therefore, the degradation products of this polymer actually aid in patient recovery. Because of pliability and ease of processing, the aromatic polyanhydrides of the present invention have great potential as polymer scaffolds for wound healing.

Example 4

Preparation of 1,3-bis(o-carboxyphenoxy)propane dicarboxylic acid 1,3-dibromopropane (14.7 ml. 0.145 mole) was added to a mixture of salicylic acid (40.0 g, 0.290 mole), distilled water (44 mL) and sodium hydroxide (23.2 g, 0.580 mole) using the method described in Example 1. After 4 hours, additional sodium hydroxide (5.79 g, 0.145 mole) was added to the reaction mixture. Reflux was continued for another 4 hours, after which the mixture was cooled, filtered and washed using the methods described in Example 1. The yield was 37.7%

Example 5

Preparation of poly(1,3-bis(o-carboxyphenoxy)propane)

The dicarboxylic acid of Example 4 was acetylated using the methods of Example 2. The acetylated dicarboxylic acid was then polymerized using the methods described in Example 3. The resulting polymer had a $M_w$ of 8,500 daltons and a polydispersity of 2.3.

Contact angle measurements on solvent-cast films demonstrated that the hexyl chain of the polymer of Example 3 increased the surface hydrophobicity relative to the shorter propyl chain of the polymer of Example 5. A comparison of thermal characteristics emphasized the effects of lengthening the alkyl chain. In particular, the polymer of Example 3 has a $T_g$ of 34° C. and a $T_d$ of 410° C., while the polymer of Example 5 had a $T_g$ of 50° C. and a $T_d$ of 344° C. Thus, the hexyl chain decreased the glass transition temperature ($T_g$) relative to the propyl chain, reflecting the increased flexibility of the polymer chain. The opposite trend was observed for decomposition temperatures ($T_d$), with the longer alkyl chain increasing the $T_d$.

Optimum polycondensation conditions were determined for the polymer of Example 3. Optimum conditions were defined as those that yielded a crude polymer with the highest molecular weight and highest $T_g$. Higher reaction temperatures decreased the $M_w$ values (measured by GPC) with a concurrent increase in polydispersity. As expected for a condensation polymerization, longer reaction times yielded polymers with higher molecular weights. However, over longer reaction times, there appeared a subsequent decrease in $T_g$. Based on these results, the optimum conditions were defined as temperatures of 220° C. for 150 minutes under a vacuum.

Example 6

Preparation of 1,8-bis[o-(benzylcarboxy)carboxyphenyl]octane dicarboxylic acid ester The initial synthesis of poly(anhydride ester) dicarboxylic acid monomers was attempted using the same methodology used for the poly(anhydride-ether) dicarboxylic monomers of Example 3. It was found, however, that the reactivity of the phenol was enhanced by benzylation of the carboxylic acid group. In addition, the solubility of benzyl salicylate in organic media increased the ability of the reaction to move forward.

Thus, benzyl salicylate (1.530 g, 6.720 mmole) and distilled tetrahydrofuran were combined under an inert atmosphere in a reaction flask. An ice-salt bath was placed under the reaction flask and the addition of 60% sodium hydride (0.4840 g, 12.10 mmole) followed. After one hour, sebacoyl chloride (0.7850 g, 3.280 mmole) was added drop-wise to the 0° C. reaction mixture. After 30 minutes, the reaction mixture was vacuum filtered, the filtrate collected and the solvent removed to yield the free carboxylate as a white solid residue. Purification was performed using a chromatron with ethyl acetate/methylene chloride (20/80) as the solvent system. The yield was 43%.

Example 7

Polymerization of Poly(1,8-bis(o-dicarboxyphenyl)octane)

To remove the benzyl protecting groups, the 1,8-bis[(benzylcarboxy)-carboxyphenyl]octane dicarboxylic acid ester of Example 6 (0.06000 g, 0.9620 mmole) was dissolved in methylene chloride in a reaction flask (60.00 mL). The catalyst Pd—C (10%, 1.200 g) was added to the reaction flask and hydrogen was bubbled through the solution. After 30 minutes, the reaction was complete. The reaction mixture was filtered and the solvent removed to yield the free dicarboxylic acid as a white solid residue which was recrystallized using petroleum ether and methylene chloride. The yield was 45%.

The dicarboxylic acid was acetylated using the methods described in Example 2 and the acetylated dicarboxylic acid was then polymerized using the methods described in Example 3. The resulting polymer had a $M_w$ of 3,000 daltons and a polydispersity of 1.40.

Subsequent polymerizations yielded polymers with $M_w$'s ranging from 2,000 to 5,000 daltons with corresponding polydispersities of approximately 1.40.

The poly(anhydride esters) of Example 7 were compression molded into circular discs and placed in phosphate buffered saline solution under acidic, neutral and basic conditions. Over the course of a three-week degradation study, the polymers in the acidic and neutral solutions showed no observable changes, whereas the polymer in the basic media showed significant morphological changes over time.

Example 8

Preparation of Poly[(1,8-bis(o-dicarboxyphenyl)octane)—(1,6-bis(p-carboxyphenoxy)hexane]copolymers The 1,8-bis(o-dicarboxyphenyl)octane of Example 2 was copolymerized with 1,6-bis(p-carboxyphenoxy) hexane using the methods described in Example 3. In an in vivo mouse study, each mouse was implanted with 2 polymers, the copolymer of Example 8 and poly(1,6-bis(p-carboxyphenoxy)hexane). Each polymer was compression molded for 1 to 5 minutes at 1 to 20 K psi depending on the thickness of polymer needed. The polymer was placed under the palatal gingival mucosa adjacent to the first maxillary molars.

All publications, patents, and patent documents (including U.S. patent application Ser. Nos. 09/455,861 and 09/508,217; as well as International Patent Application PCT/US98/118816) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to decrease bone resorption or to promote healing of bone at a site in the body of a patient comprising, administering an effective amount of an anti-inflammatory agent at or near the site, wherein the agent is incorporated into the backbone of a biodegradable polymer wherein the polymer is a polyanhydride comprising a repeating unit having the structure:

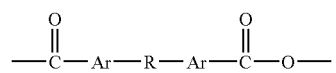

wherein Ar is a subtituted or unsubstituted aromatic ring and R is —$Z_1$—$R_1$—$Z_1$ substituted on each Ar ortho to the anhydride group, wherein $R_1$ is a difunctional organice moiety and $Z_1$ is a difunctional moiety selected from the group consisting of esters, amides, carbamates and carbonates.

2. The method of claim 1 which is a method to decrease bone resorption.

3. The method of claim 1 which is a method to promote healing of bone.

4. The method of claim 1 wherein the agent is a salicylate.

5. The method of claim 1 wherein the agent is a nonsteroidal anti-inflammatory compound.

6. The method of claim 1 wherein the agent is a cyclooxygenase inhibitor.

7. The method of claim 1 wherein the agent is a cyclooxygenase-1 inhibitor.

8. The method of claim 1 wherein the agent is a cyclooxygenase-2 inhibitor.

9. The method of claim 1 wherein the agent is formulated for controlled release at the site.

10. The method of claim 1 wherein the agent is administered after periodontal surgery.

11. The method of claim 1 wherein each $Z_1$ is an ester.

12. The method of claim 11 wherein the agent is salicylic acid.

13. The method of claim 1, wherein Ar and R are selected so that hydrolysis of the polyanhydride provides the anti-inflammatory agent.

14. The method of claim 13, wherein Ar is a phenyl group.

* * * * *

UNITED STATES PATENT AND TRADEMARK OFFICE
CERTIFICATE OF CORRECTION

PATENT NO. : 8,088,405 B2
APPLICATION NO. : 11/524664
DATED : January 3, 2012
INVENTOR(S) : Uhrich Page 1 of 1

It is certified that error appears in the above-identified patent and that said Letters Patent is hereby corrected as shown below:

In the Claims

In Column 18, Line 21, Claim 1

Replace:

organice

With:

organic

Signed and Sealed this
Thirtieth Day of July, 2013

Teresa Stanek Rea
*Acting Director of the United States Patent and Trademark Office*